(12) United States Patent
Walch

(10) Patent No.: US 7,922,649 B2
(45) Date of Patent: Apr. 12, 2011

(54) UNITIZED PENILE ERECTION SYSTEM AND TISSUE EXPANDER

(76) Inventor: John R. Walch, Egg Harbor Township, NJ (US)

( * ) Notice: Subject to any disclaimer, the term of this patent is extended or adjusted under 35 U.S.C. 154(b) by 426 days.

(21) Appl. No.: 12/221,962

(22) Filed: Aug. 8, 2008

(65) Prior Publication Data
US 2010/0036196 A1 Feb. 11, 2010

(51) Int. Cl.
*A61F 5/00* (2006.01)
(52) U.S. Cl. ........................................................ 600/40
(58) Field of Classification Search ............... 600/38–41
See application file for complete search history.

(56) References Cited

U.S. PATENT DOCUMENTS

| | | | | |
|---|---|---|---|---|
| 4,267,829 A | | 5/1981 | Burton et al. | |
| 4,353,360 A | | 10/1982 | Finney et al. | |
| 4,369,771 A | | 1/1983 | Trick | |
| 4,572,168 A | | 2/1986 | Fischell | |
| 4,594,997 A | | 6/1986 | Hakky | |
| 4,665,903 A | | 5/1987 | Whitehead | |
| 4,791,917 A | * | 12/1988 | Finney | 600/40 |
| 4,807,608 A | * | 2/1989 | Levius | 600/40 |
| 5,067,485 A | | 11/1991 | Cowen | |
| 5,129,880 A | | 7/1992 | Grundei | |
| 5,167,611 A | * | 12/1992 | Cowan | 600/40 |
| 5,250,020 A | | 10/1993 | Bley | |
| 5,468,213 A | * | 11/1995 | Polyak | 600/40 |
| 5,669,870 A | | 9/1997 | Elist | |
| 5,788,627 A | | 8/1998 | Subrini | |
| 2005/0014993 A1 | * | 1/2005 | Mische | 600/40 |
| 2008/0103353 A1 | * | 5/2008 | Jahns et al. | 600/40 |

* cited by examiner

*Primary Examiner* — John P Lacyk
(74) *Attorney, Agent, or Firm* — Norman E. Lehrer

(57) ABSTRACT

A surgically implantable device is a single unit comprised of a hydraulically activated extendable cavernosal component and a manually controlled fluid transfer system composed of a pump. Flow from the pump is directed by a one way valve interposed between a bypass from an included elastic reservoir, the pump and a second one way valve interposed between the pump and the cavernosal unit. A manually controlled release valve, interposed between the outlet of the cavernosal unit and the reservoir, permits de-activation of the cavernosal unit and returns fluid to the reservoir. These components are housed by a molded tailpiece which stabilizes the device against the symphysis pubis, positions the cavernosal implant properly within the shaft of the penis and presents the controls for easy access. An access port permits adjustment of the fluid volume. The unit has utility as a tissue expander and penile re-construction in event of congenital or traumatic deformity.

8 Claims, 4 Drawing Sheets

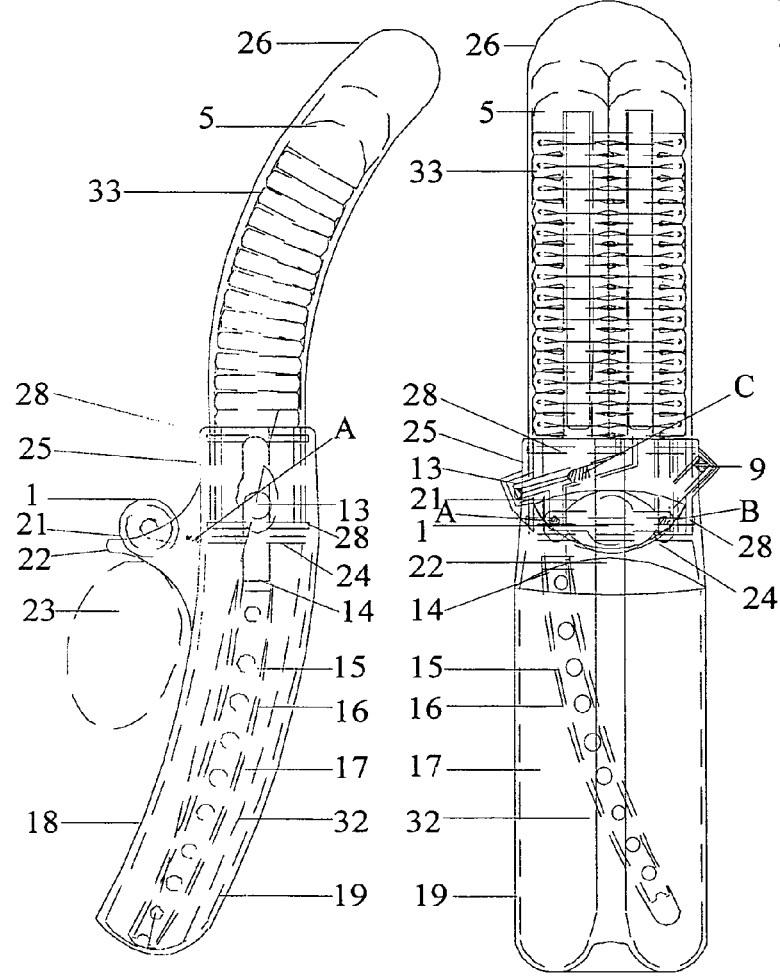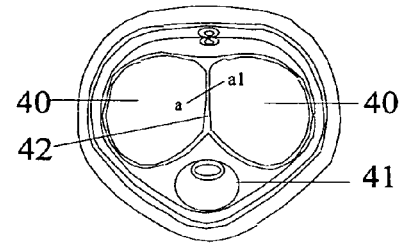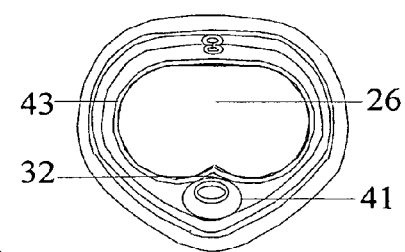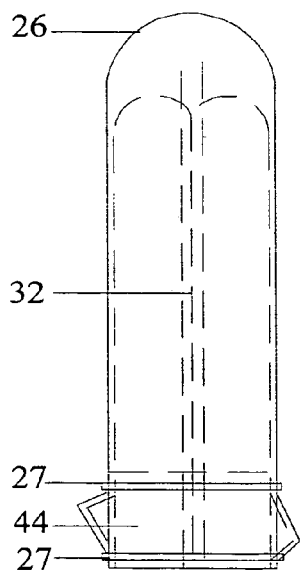
Fig. 1
Fig. 2
Fig. 3
Fig. 4
Fig. 5

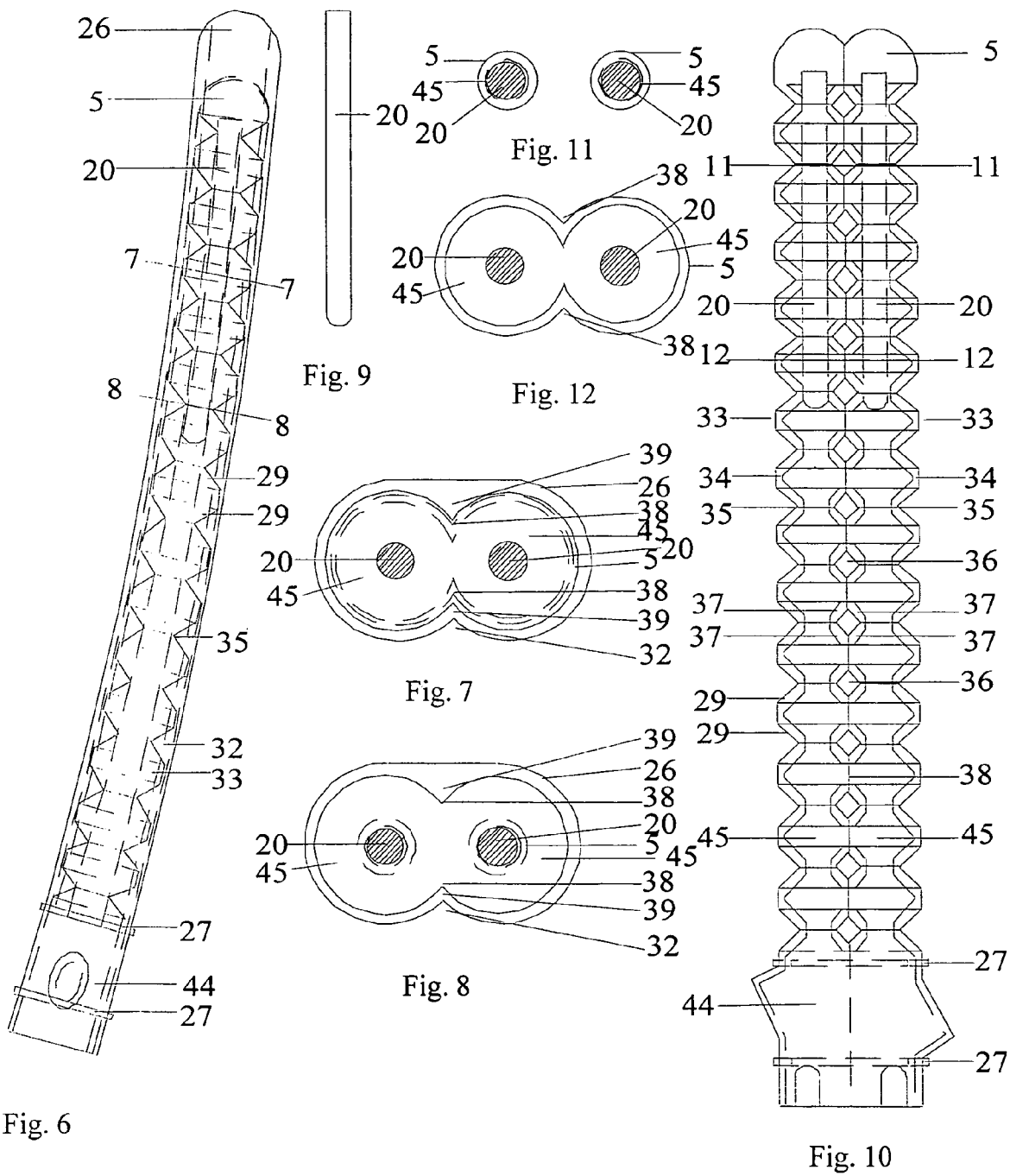

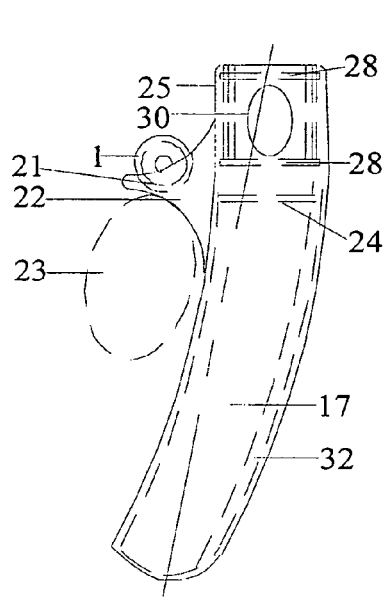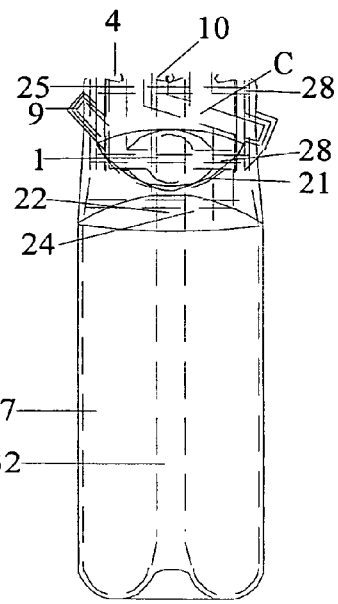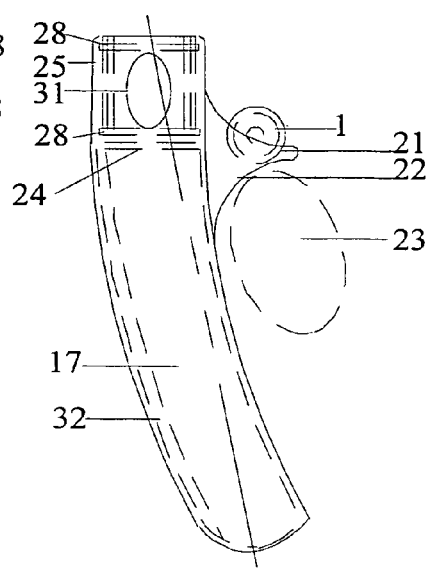
Fig. 13　　　　　Fig. 14　　　　　Fig. 15
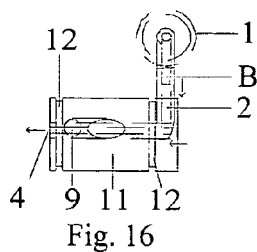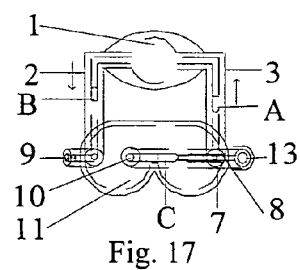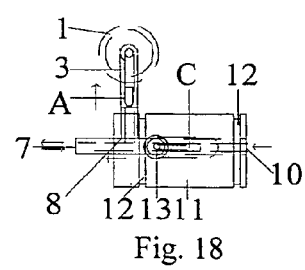
Fig. 16　　　　　Fig. 17　　　　　Fig. 18
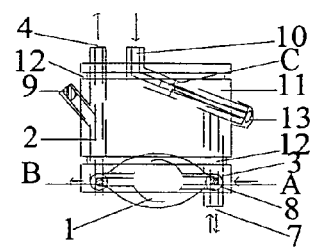
Fig. 19

UNITIZED PENILE ERECTION SYSTEM AND TISSUE EXPANDER

FIELD OF THE INVENTION

The present invention relates to systems for treating erectile dysfunction and other urological disorders in the human male. In particular, the invention relates to implantable penile prostheses.

BACKGROUND OF THE INVENTION

The evolution of the interventional treatment of erectile dysfunction has a colorful history. Initial attempts centered around external splints. Overlapping efforts then included trusses and external constriction about the root of the male organ and vacuum devices designed to fill the organ passively combined with a circular constrictor, again placed at the root of the male organ.

Surgically implantable sphincter systems with inflatable constrictors placed at the root of the organ or each arm of the cavernosa have also been offered. Additional ideas included implantable rigid rods and malleable rods. Commensurate with these, various hydraulically activated fully implantable devices requiring multiple insertion sites show a multiplicity of designs. Many associated devices and related implements have also been presented to support such systems.

One known type of penile implant device, for example, includes a pair of cylindrical prostheses that are implanted into the corpus cavernosae of the penis. The prostheses are inflatable and are connected to a fluid-filled reservoir through a pump and valve assembly. Such a pump assembly is typically implanted into the scrotum of the patient, and the reservoir is implanted in the abdomen. To activate the penile implant device, the patient actuates the pump using one of a variety of methods that cause fluid to be transferred from the reservoir through the pump and into the prostheses. This results in the inflation of the prostheses and produces rigidity for an erection. Then, when the patient desires to deflate the prostheses, a valve assembly within the pump is actuated in a manner such that the fluid in the prostheses is released back into the reservoir. This deflation returns the penis to a flaccid state.

The surgical approach to erectile dysfunction has inherent risks including the erosion of the tissues surrounding the devices when constant pressure due to the rigidity of the device is applied to these tissues. A second risk is that of infection, a great deal of which is related to handling of the scrotal tissues required for the remote implantation of devices, the scrotum being in close proximity to the perineal structures and anal region which is difficult to sanitize for surgical procedures. Placement of a remote reservoir within the pre-peritoneal and/or the intra-abdominal cavities carries the risks of intra-abdominal infection, bowel erosion or obstruction, adhesive compression of the reservoir and all connections are at risk of leak or disconnection. In addition, the routing of tubing from element to element is also a source of long term discomfort to the user.

Any surgical implantation will include the risk of intra-operative or post-operative bleeding. Elimination of multiple surgical sites can reduce this risk substantially, the skill and technique of the implanting surgeon being the final, but uncontrollable factor. The limiting factor of hydraulic implants has been the amount of fluid required to initiate a substantial erection and the storage of that fluid when the erectile unit is decompressed. This required volume, heretofore, has required a rather voluminous reservoir.

More recently, unitized devices have been proposed which contain the necessary elements to initiate an erection without the necessity of implantation of remote reservoirs or inflation pumps and the associated tubing required to connect these elements. While these devices may reduce many of the surgical risks described above, because of their design, there is insufficient fluid volume to allow the implant to operate properly.

Therefore, a need exists for a unitized implantable erectile device that requires a much reduced volume of fluid that can be stored within the unitized device without significantly restricting the final length of the erect implant.

SUMMARY OF THE INVENTION

The present invention is designed to overcome the deficiencies of the prior art discussed above. Accordingly, it is an object of the invention to provide a unitized implantable inflatable prosthetic penile device or system.

It is a further object of the present invention to provide a unitized implantable inflatable prosthetic penile device or system that requires a smaller volume of fluid transfer to inflate the prosthesis.

It is a still further object of the invention to provide a unitized implantable inflatable prosthetic penile device or system that requires a smaller volume of fluid transfer to inflate the prosthesis and that provides a more natural and full feel of the penis in its flaccid state.

In accordance with the illustrative embodiments demonstrating features and advantages of the present invention, there is provided a unitized surgically implantable device comprised of a hydraulically activated extendable cavernosal component and a manually controlled fluid transfer system composed of a pump. Flow from the pump is directed by a one way valve interposed between a bypass from an included elastic reservoir, the pump and a second one way valve interposed between the pump and the cavernosal unit. A manually controlled release valve, interposed between the outlet of the cavernosal unit and the reservoir, permits de-activation of the cavernosal unit and returns fluid to the reservoir. These components are housed by a molded tailpiece which stabilizes the device against the symphysis pubis, positions the cavernosal implant properly within the shaft of the penis and presents the controls for easy access. An access port permits adjustment of the fluid volume. The unit has utility as a tissue expander and penile re-construction in event of congenital or traumatic deformity.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 1 is a right side sectional view of the unitized device of the present invention in the semi-flaccid position demonstrating the internal extender unit in phantom view within the outer sheath, the tailpiece with an offset shelf to position and stabilize the unit against the sysmphysis pubis, which is shown in outline, and to position the bulb pump for access, and depicting the fluid transfer system in phantom outline;

FIG. 2 is a bottom view of the unitized device in the compressed position demonstrating the internal extender unit in phantom outline within the outer sheath and the relationship of the release valve, bulb pump, access port and the elastic reservoir and scavenger tube within the confines of the tailpiece;

FIG. 3 is a cross-sectional view of the human male penis depicting the major structures, the most significant of which is the fascial outline of the paired corpus cavernosae, the septal structure formed by the approximation of the medial surfaces and the proposed incision plane (a-a1) of the septum to transform the cavernosal compartments into a single space to receive the prosthetic unit within the shaft of the penis;

FIG. 4 is a cross-sectional view of the human male penis depicting the outline of the modified cavernosal fascia containing the cross-sectional outline of the prosthesis and its proposed relationship to the structures of the penile shaft;

FIG. 5 is a top view of the decompressed outer sheath separated from the inner extender depicting the relationship of its features;

FIG. 6 is a right side view of the internal cavernosal extender in phantom outline and the outer sheath in the extended erection position demonstrating the position of the release valve on the presenting aspect and the position of the access port in phantom outline on the opposite side, and depicting in phantom outline a volume reducer of solid silicon elastomer located within the distal end of the internal unit;

FIG. 7 is a cross sectional view of the sheath and extender unit taken at the line indicated by 7-7 on FIG. 6 and demonstrating the relationship of the outer sheath to the extender at it's widest aspect and the contained volume reducer;

FIG. 8 is a cross sectional view of the sheath and extender unit taken at the line indicated by 8-8 on FIG. 6 and demonstrating the relationship of the outer sheath to the extender at it's narrowest aspect and the contained volume reducer;

FIG. 9 is a longitudinal view of one of the paired, solid, cylindrical elastomeric volume reduction units which are fused within the distal lumen of the extender unit on either side;

FIG. 10 is a top view of the internal extender unit in the erect extended position containing a phantom view of the volume reducers within the distal end, the relative position of the access port on the left side of the unit and the release valve position to the right, which region represents a chamber designed to house the fluid transfer system and depicting the compression aperture formed between the individual expansion segments which serves to assist in compression of the device and to prevent ballooning of the device when distended under pressure.

FIG. 11 is a cross-sectional view of the cavernosal implant taken at the line indicated by 11-11 on FIG. 10 and demonstrating the features and relationships between the inner extender unit and the volume reducers at the level of the constricted connecting region of each extension segment;

FIG. 12 is a cross-sectional view of the cavernosal implant taken at the line indicated by 12-12 on FIG. 10 and demonstrating the features and relationships between the inner extender unit and the volume reducers at the wider profile of the individual extension segments;

FIG. 13 is a left side view of the assembled tailpiece depicting the offset position of the bulb pump and the formed curvature of the upper surface to mate and stabilize against the sysmphysis pubis shown in phantom outline;

FIG. 14 is a top view of the two piece tailpiece demonstrating the position of the access port on the left side of the unit, the offset bulb pump and the release valve located in the region of the cavernosal perch designed to stabilize the cavernosal unit within the tailpiece, which also contains the transfer system including the elastic reservoir;

FIG. 15 is a right side view of the assembled tailpiece depicting the offset position of the bulb pump and the formed curvature of the upper surface to mate and stabilize the implant against the sysmphysis pubis which is shown in phantom outline;

FIG. 16 is a left side view of the assembled fluid transfer system less the elastic reservoir assembly with arrows depicting the direction of flow within the system;

FIG. 17 is a proximal end view of the assembled fluid transfer system less the elastic reservoir assembly with arrows depicting the direction of flow within the system;

FIG. 18 is a right side view of the assembled fluid transfer system less the elastic reservoir assembly with arrows depicting the direction of flow within the system;

FIG. 19 is a top view of the assembled fluid transfer system less the elastic reservoir assembly with arrows depicting the direction of flow within the system;

DETAILED DESCRIPTION OF THE PREFERRED EMBODIMENT

Figures 20, 21:
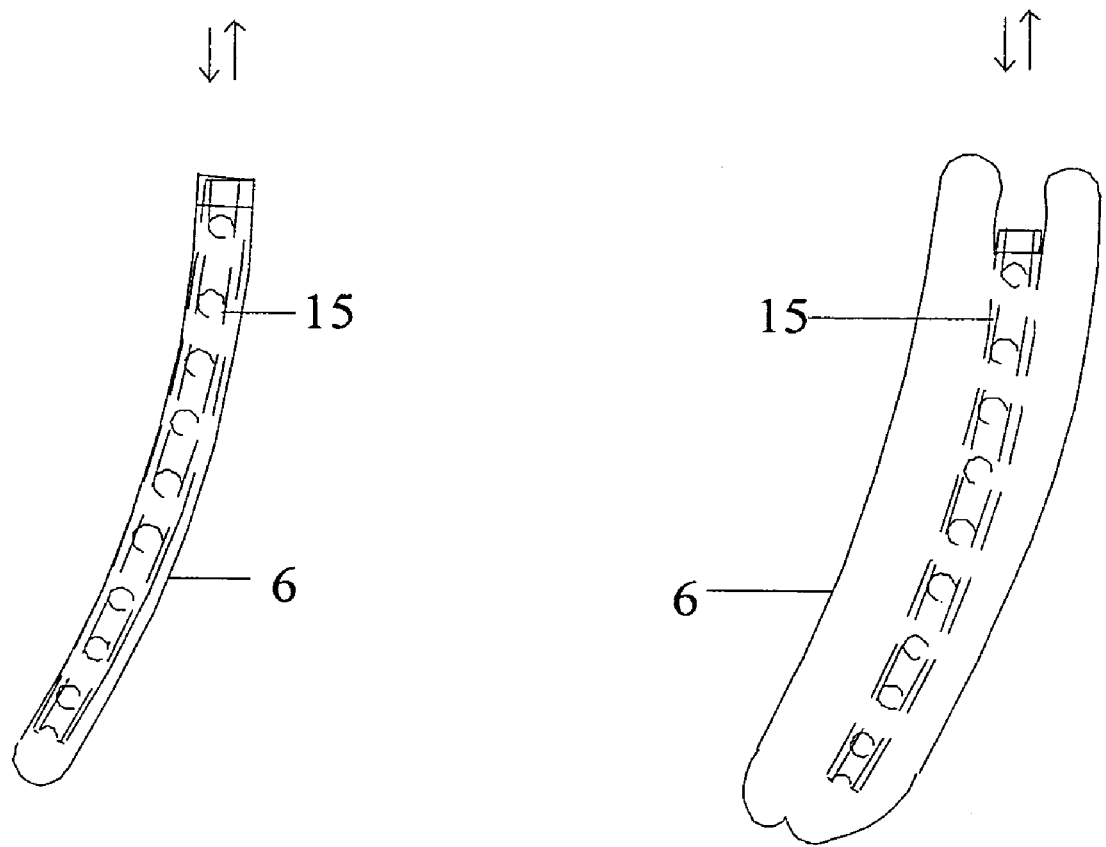
FIG. 20 is a side view of the perforated scavenger tube and the empty elastic reservoir assembled to depict the reservoir component with arrows depicting the direction of flow within the system.
FIG. 21 is a side view of the assembled scavenger tube and the elastic reservoir in the partially filled position with arrows depicting the direction of flow within the system.

Referring now to the drawings in detail wherein like reference numerals have been used throughout the various figures to designate like elements, there is shown in FIGS. 1 and 2 a unitized implantable inflatable prosthetic penile device or system constructed in accordance with the principles of the present invention. The implantable penile device as depicted in a right lateral aspect in FIG. 1 has been designed to be placed in an anatomical position in relation to the symphysis pubis 23 that corresponds to the normal position of the corpus cavernosum 40, corpus spongiosum 41, and the anchoring crura of the cavernosal system which are located below the sysmphysis pubis 23, and follows along the bony ischial rami of the male pelvis. (See FIGS. 3 and 4.)

Referring to FIG. 3, it can be seen that the fused, unitized design of the invention would require incision, designated by line a-a1, of the fascial septae of the adjacent cavernosal fascial compartments 42 surrounding the paired cavernosae thereby forming a single compartment designated the combined cavernosal cavity 43, as shown in FIG. 4, for longitudinal placement of the cavernosal implant 26 within the shaft of the male penis.

As shown in FIG. 4, the fused ovoid cross section of the cavernosal implant 26 requires either excision or displacement of the vascular structures of the corpus cavernosae 40 to allow placement within the modified combined cavernosal cavity 43. The urethral groove 32 of the lower surface of the cavernosal unit 26 allows for the unobstructed position of the urethra and corpus spongiosum 41 so as not to interfere with urination or ejaculation.

Referring now to FIG. 17, digital compression of the bulb pump 1 will direct flow of the hydraulic fluid within the fluid transfer system by amplifying the closure of inlet valve A within the inlet channel 3 and effecting opening of valve B within the outlet channel 2. The fluid is then directed through valve B and into extender inlet channel 4 and then flows into the common lumen 45 of the inner extender unit 5. Releasing the digital pressure permits re-expansion of the bulb pump 1 and concomitant closure of valve B. The negative pressure generated by the re-expansion of the bulb pump 1 causes valve A to open and the negative pressure within the bulb pump 1 combined with the low but positive pressure generated within the distended elastic reservoir 6 causes the flow of the hydraulic fluid from the elastic reservoir 6 through the reservoir inlet-outlet port 7 which will then direct the forward flow of the hydraulic fluid through the pump bypass junction 8 through the inlet channel 3 past valve A and subsequently into the bulb pump 1, which, when full, is ready to repeat the cycle until the inner extender unit 5 has reached it's maximal length or the optimal length permitted by the elasticity of the tissues of the penis into which the unit has been implanted.

Referring again to FIG. 19, a side arm access port 9 with a self-sealing membrane and connecting to the extender inlet channel 3 permits the addition or withdrawal of hydraulic fluid to customize the overall length of the implant as determined by the surgeon either at the time of implantation or postoperatively when indicated and prudent. Withdrawal of inadvertently injected air is also made possible through this port which is forward directed for the ease of access by the clinician.

The access port 9, extension unit inlet 4, extension unit outlet 10 and the manually controlled release valve C are sealed within the transfer system main seal 11 into which are also molded positioning seal grooves 12 which correspond with internal seal ridges 27 molded within the transfer system chamber 44 located within the inner extender unit 5. The fluid transfer system, FIG. 16, positions the manual release control rod 13 in a rearward direction so that inadvertent release from surrounding tissue pressure is avoided. The access port 9 presents the injection membrane in a forward direction to make needle insertion accurate and safe.

Deactivation of the extended unit is initiated by depression of the manual release control rod 13 sealed within the housing of the release valve C interposed between the extender outlet channel 10 and subsequently directing the fluid flow past the pump bypass junction 8 and into the reservoir inlet/outlet port 7 traversing the transfer system/reservoir connection 14 and finally into the perforated scavenger tube 15 and the elastic reservoir 16 which are located within the cavity 17 of the tailpiece 18,19.

In regard to the volume of hydraulic fluid required to acquire maximal extension, the inner cavity 45 of the fully extended inner unit 5 displaces less than 20 cc of fluid. The addition of the paired cylindrical volume reducers 20 into the lumen 45 of the extender unit 5 reduces the volume demand even further. The volume of the tailpiece cavity 17 exceeds 20 cc of fluid. The additional volume of available fluid permits a turgid erection. If implanted for reconstruction, the extremes of compression permit implantation into anatomically small organs. The ability to manually control the overall length of the erection permits institution of a monitored program of repeated extension and decompression with increasing length of extension in a controlled manner which, over time should effect erectile enlargement of the implanted organ.

When the fluid transfer system, FIG. 16-19, is assembled within the fluid transfer chamber 44 of both the extender unit 5 and the outer sheath 26 forming the cavernosal implant and the combined pieces are mated to the tailpiece, several aspects of the construction should be noted. The bulb pump 1 is set within a recessed perch 21 that is supported by the symphyseal perch 22 which has been designed to abut against the symphysis pubis 23 which positions and stabilizes the entire unit after implantation. In conjunction with a solid internal cavernosal buttress 24 forming the floor of the cavernosal perch 25 which seats the cavernosal implant 26 and reinforces the location system which consists of a series of seal ridges 27 and corresponding seal grooves 28 which not only position the individual pieces of the cavernosal prosthesis 26 but interlock and provide additional surface area for application of sealing adhesives.

When the fluid transfer system, FIGS. 16-19, is installed within the provided chambers of the inner extender unit 5 and outer sheath 29 and the assembled unit is placed within the cavernosal perch 25, the manually controlled release valve 13 is then positioned within an aperture provided, the release valve aperture 30, FIG. 13, and positions the access port 9 within a similar access port aperture 31, FIG. 15. As with the design of the cavernosal prosthesis 26, the tailpiece has a urethral groove 32 molded into the surface of the lower tailpiece casing 19 to prevent displacement, obstruction or injury to the urethral structures after the prosthesis has been implanted.

As shown most clearly in FIGS. 10, 11 and 12, the inner extender unit 5 has specific and unique design features. The serial extender segments 33 have the ability to compress and expand while requiring only approximately 0.6 cc of internal fluid volume for expansion of an individual segment. The accordion-like function is accomplished with the assistance of two separate features. The outer periphery of each segment is molded into a thinned region, the flexion hinge 34. When expanded or compressed, the flexion hinge 34 permits easy movement of the sidewalls 29 of each segment. The side walls 29 are thick and relatively inflexible as compared to the thinned flexion hinges 34.

Within the constricted region of each segment 33, the connection is also more deeply grooved to form a thinned inner extension hinge 35. This increases the ability to flex during expansion or compression. At the region of the constricted area, the fusion of the two cylindrical halves forms the compression aperture 36 which enhances compression of the segments 33, one upon the other, thereby minimizing the compressed length of the inner extender unit 5. This flexibility is also manifest by the ability of the unit to assume the dependent position due to gravitational force. The confluence of material centrally around the compression aperture 36 forms a stabilizing structure, the lateral expansion suppressor 37, which serves to inhibit lateral expansion or ballooning.

The discoid appearance of the compressed segments joined centrally to have essentially a FIG. 8 appearance accomplishes several things. The first of which is that the internal cavity of each half is continuous with the other forming the inner extender lumen 45 and serves to equalize the internal extension pressure and ensuring equal extension of each side. This occurs, of course, due to the openings in the walls of each of the tubular channels where they are connected (see FIG. 12) so that fluid flows between them at numerous positions along the length thereof. The cylindrical shape of each half centrally joined forms the guide grooves 38 located along the length of the upper and lower surfaces of the inner extender unit 5 and serve to track along the guide ridges 39 located longitudinally within the lumen of the outer sheath 26 to provide additional lateral stability to the unit when extended.

The thick walls 29 of the expansion segments 33 also assist in prevention of ballooning and are resistant to flexion secondary to the internal pressure required to activate the inner extender unit 5. The thick walls 29 also serve to limit the amount of fluid required to maximally extend the unit.

The outer sheath 26 is designed to encase the inner extender 5. The stretching of the outer sheath increases the tension along the walls which also serves to contain and restrict the inner unit and reduce lateral expansion some of which is desirable during erection but counterproductive in the face of a limited reservoir volume.

The present invention may be embodied in other specific forms without departing from the spirit or essential attributes thereof and accordingly, reference should be made to the appended claims rather than to the foregoing specification as indicating the scope of the invention.

I claim:

1. In a unitized implantable penile prostheses including an hydraulically activated extendable cavernosal component and a manually controlled fluid transfer system composed of a pump and valve means and wherein said extendable component includes an extendable inner unit and wherein the extendable inner unit is convertible from a flaccid condition to a rigid condition when a sufficient volume of fluid is transferred into the extendable inner unit to substantially fill the same, the improvement comprised of said extendable inner unit being formed by a pair of parallel tubular channels adapted to contain said fluid therein, said channels being defined, at least in part, by walls that extend in an accordion fashion and which have alternating wider and narrower segments, said walls of said pair of parallel tubular channels being connected at multiple locations along at least a major portion of the length thereof at positions of wider segments, said walls of each tubular channel having openings therein at the locations where they are joined with the other tubular channel to allow fluid to flow between the interiors of the pair of the channels at said locations thereby forming a single expandable internal lumen having a substantially figure 8 shaped cross-section.

2. The improvement as claimed in claim 1 wherein said walls include a multiplicity of grooves therein along the outer periphery forming flexible areas in said walls.

3. The improvement as claimed in claim 1 further including a pair of cylindrically shaped volume reducers within said internal lumen and located only within the distal end thereof.

4. The improvement as claimed in claim 1 further including a single outer extendable sheath surrounding both of parallel tubular channels comprising said extendable component including the distal ends thereof 5. The improvement as claimed in claim 1 wherein said extendable component includes a urethral groove on the outer surface thereof to allow for the unobstructed position of the urethra and corpus spongiosum so as not to interfere with urination or ejaculation after the prosthesis has been implanted.

6. The improvement as claimed in claim 1 wherein said manually controlled fluid transfer system is contained within a casing connected to said extendable component.

7. The improvement as claimed in claim 6 wherein said a casing includes a urethral groove formed in the outer surface thereof to prevent displacement or obstruction or injury to the urethral structures after the prosthesis has been implanted.

8. The improvement as claimed in claim 3 wherein said pair of cylindrically shaped volume reducers is comprised of solid silicon elastomer.

* * * * *